(12) United States Patent
Hueber

(10) Patent No.: US 7,994,077 B2
(45) Date of Patent: Aug. 9, 2011

(54) UV-TRANSMISSION FABRIC, METHOD OF OBTAINING THE SAME AND GARMENT BEING MADE OF THE SAID FABRIC

(76) Inventor: Antonius Gerardus Maria Egidius Hueber, GG Grubbenvorst (NL)

( * ) Notice: Subject to any disclaimer, the term of this patent is extended or adjusted under 35 U.S.C. 154(b) by 43 days.

(21) Appl. No.: 12/446,848

(22) PCT Filed: Dec. 15, 2006

(86) PCT No.: PCT/EP2006/012140
§ 371 (c)(1),
(2), (4) Date: Apr. 23, 2009

(87) PCT Pub. No.: WO2008/071224
PCT Pub. Date: Jun. 19, 2008

(65) Prior Publication Data
US 2010/0033809 A1    Feb. 11, 2010

(51) Int. Cl.
*D04B 1/00* (2006.01)
*D04B 11/00* (2006.01)
*D04B 21/00* (2006.01)

(52) U.S. Cl. ........ 442/304; 442/306; 442/414; 428/332; 428/340

(58) Field of Classification Search ............... 442/304, 442/306, 414; 428/332, 340
See application file for complete search history.

(56) References Cited

U.S. PATENT DOCUMENTS

| | | | | |
|---|---|---|---|---|
| 4,115,615 A | * | 9/1978 | de Buck van Overstraeten | 442/60 |
| 4,546,493 A | | 10/1985 | Bortnick | |
| 4,793,668 A | * | 12/1988 | Longstaff | 359/361 |
| 4,798,427 A | | 1/1989 | Sear | |
| 5,066,082 A | * | 11/1991 | Longstaff | 359/361 |
| 5,414,913 A | * | 5/1995 | Hughes | 26/29 P |
| 5,518,798 A | | 5/1996 | Riedel | |
| 7,555,922 B1 | * | 7/2009 | Berlin | 66/195 |
| 2004/0224582 A1 | | 11/2004 | Kroll | |

FOREIGN PATENT DOCUMENTS

| | | |
|---|---|---|
| WO | 9323222 A | 11/1993 |
| WO | 0011981 A | 3/2000 |
| WO | 2004085734 A | 10/2004 |
| WO | 2004090589 A | 10/2004 |

* cited by examiner

*Primary Examiner* — Norca L Torres-Velazquez
(74) *Attorney, Agent, or Firm* — Richard M. Goldberg

(57) ABSTRACT

A fabric includes a first yarn having a UV-A transmission of between 10 and 50% while substantially blocking UV-B transmission, and at least a second yarn different from the first yarn, the yarns being interweaved such that the fabric has regular mesh openings that give rise to a transmission of the fabric of between 20 and 65% for UV-A and between 3 and 20% for UV-B.

19 Claims, 2 Drawing Sheets

UV-TRANSMISSION FABRIC, METHOD OF OBTAINING THE SAME AND GARMENT BEING MADE OF THE SAID FABRIC

BACKGROUND OF THE INVENTION

The invention pertains to a UV transmissive fabric that has a transmission of between 20 and 65% for UV-A and between 3 and 20% for UV-B. The invention also pertains to a method of manufacturing such a fabric and a garment being made by using the fabric.

EP-0 267 655 B1 discloses a UV-filter of the type indicated above, which may be in the form a warp-knitted fabric of polyester fibres and is suitable for protecting human skin from the damaging effects of excessive exposure to solar radiation while permitting immediate pigment tanning and encouraging the de-novo melanin synthesis. To this end, the known filter is essentially transmissive to ultra violet radiation in the UV-A range (320-400 nm), while it is essentially opaque for ultraviolet radiation in the UV-B range (290-320 nm). However, a certain leakage of UV-B radiation is said to be desirable for stimulating the melanocytes to produce greater quantities of new Melanin, which will then be available for tanning by UV-A.

Although the known fabric is suitable for constituting e.g. a screen that allows people to get tanned while decreasing the risk of severe sunburn, this fabric is limited in applicability given its specific mechanical and colouring properties. It is for example not suitable for making comfortable and appealing outerwear.

SUMMARY OF THE INVENTION

It is therefore an object of the invention to provide a fabric that has adequate UV-transmission characteristics to enable skin tanning and still have a relatively high sun (or solar) protection factor (commonly known as SPF), which fabric is less limited in applicability.

To this end a fabric has been provided comprising a first yarn having a UV-A transmission of between 10 and 50% while substantially blocking UV-B transmission, and at least a second yarn different from the first yarn, the yarns being interweaved such that the fabric has regular mesh openings that give rise to the required transmission characteristics.

The invention started off with the recognition that in the prior art fabric, the yarn used must provide all relevant properties to the fabric, i.e. the UV-transmission properties as well as the mechanical properties and the susceptibility to dyes. Since the UV-transmission characteristics are essential for the fabric, the other properties are often a mere outcome, or at least there is a very limited freedom in choice for these properties. Based on that recognition, applicant realised that the freedom of choice could be greatly enhanced when the properties of the fabric can be controlled more independently from each other. This lead to the first feature of the invention, namely taking a yarn that meets restricted UV transmission characteristics, i.e. between 10 and 50% for UVA while substantially blocking (either by absorption or reflection or a combination of both) UV-B transmission. Blocking in the sense of this invention means a transmission of up to approximately 5% for UVB. A typical transmission for a suitable yarn is between 0 and 3% for the UVB between 290 and 310 nm (which is the most harmful part of the UVB radiation). At first sight this substantial UVB blocking might seem contradictory to the necessary transmission properties of the ultimate fabric. However, it was applicants merit to realise that an adequate transmission of the fabric for UVA (between 20 and 65%) and UVB (between 3 and 20%) can still be provided by taking a second yarn, and interweaving (for example by weaving or knitting) both yarns such that regular mesh openings arise for obtaining the proper UV transmission of the fabric. Given the fact that the UV transmission properties of the first yarn are quite strict, the UV transmission properties of the second yarn do not have to meet stringent demands. Most materials for making yarns, either synthetic or natural, essentially block UVA as well as UVB. However, by using at least this second yarn for making the fabric, even if this yarn totally blocks UV radiation, the transmissiveness of the fabric can be increased (instead of limited) when compared to the transmissiveness of the first yarn, simply by providing the regular mesh openings. On the other side, if for example a second yarn would be used that has a very high transmissiveness for UVA (e.g. over 60%) and UVB (e.g. over 20%), adequate transmissiveness for the fabric can still be obtained by applying an adequate (not too high) amount of the second yarn and relatively small mesh openings.

The application of at least one other yarn next to the first yarn means that the ultimate properties of the fabric are determined also by the properties of the second yarn. Moreover, by starting off with a first yarn with the very restricted UV transmission properties as indicated here-above, there is a great freedom in choice for the second yarn, thus enabling the skilled practitioner to provide an extended range of properties, in particular mechanical and colouring properties, for the ultimate fabric. Moreover, since the UV-transmission properties can be controlled more precisely, it has been found that favourable UV-A transmission properties of between 25 and 60% and between 5 and 15% for UV-B can be provided for the fabric. In particular, when applying the present invention a fabric can be provided having a UV-A transmission between 30 and 45% and a UV-B transmission between 10 and 12%. The latter fabric has an SPF of about 8 while still providing very good skin tanning. Such properties can be advantageously provided preferably with a first yarn having an UV-A transmission of between 20 and 50%, most preferably about 30%.

In an embodiment the second yarn is a non-elastic yarn. Non-elastic in the sense of this patent means that the yarn cannot be reversibly elongated more than 5% in length. This embodiment can lead to a fabric that is very suitable for loosely worn outerwear such as shirts, shorts, skirts, dresses etc. In a further embodiment, the first and second yarns are interweaved via a double-knitting process. The double knitted fabric or double Jersey having a certain amount of e.g. natural non-elastic yarn such as cotton, is favourable for use as a garment, especially for outerwear, in terms of its improved strength, grip, texture and appearance and in terms of its heat insulation and wind protection properties and its ability to absorb human sweat. The inventor has found that it is possible to configure such a double Jersey so as to fulfil the UV transmission requirements, in spite of the relatively close bonding structure and the presence of second yarn which is essentially non-transparent to both UV-A and UV-B. In an embodiment the content of the non-elastic yarn is between 15 and 85%, preferably between 50 and 60%, based on the total weight of the fabric. This way a very broad range of mechanical and colouring properties is provided while still being able to meet the UV-transmission properties by providing an adequate regular mesh structure. Preferably the weight of the fabric is between 90 and 180 $g/m^2$, more preferably between 125 and 150 $g/m^2$. In particular at a weight of approximately 130 g/m2, a non- or hardly transparent fabric (i.e. with respect to visible light) can be provided that still meets the UV-transmission demands (for example by deliberately dropping stitches in the double-knitting process).

In an alternative embodiment the second yarn is an elastic yarn. In this embodiment a fabric is provided that is typically worn while being stretched to a certain amount, typically up to 15%, such as swim- and bikewear. In an embodiment the second yarn is a naked yarn (i.e. not covered with another yarn), typically giving rise to a more or less coil-like fibre structure, and the content of the second yarn is between 10 and 30%, preferably around 20%, based on the total weight of the fabric. When the content of the second yarn is more than 30% it appears that the UV-transmission demand cannot be reasonably met. In particular, the transmission factors will generally be too low. By applying a content less than 30%, preferably around 20%, a fabric can be provided that is very suitable for outerwear that is typically worn under stretch conditions. In an embodiment the fabric contains 30-50% of the first yarn, and up to 60% of a third yarn, the third yarn being non-elastic.

In another embodiment that the second yarn is an elastic corespun yarn. A corespun yarn is a yarn wherein the core is covered with a second yarn (see also ASTM Method D123). Such yarns are commonly known and for example described in U.S. Pat. No. 5,303,550. It appears that by using a corespun yarn, smaller and/or fewer meshes can be used while still being able to obtain sufficient UV-A and UV-B transmissiveness. This is advantageous e.g. because higher weights of the fabric can be used. Such a fabric can be less transparent for visible light (also depending on the colour of the dyestuff) which for many applications is more appealing to wearers. It even appears that fabrics which are worn under very low stretch conditions can still have sufficient UV transmissiveness features despite the fact that they are hardly stretched out. It appears that a fabric according to this embodiment is very suitable for outerwear that is worn under low stretch conditions, typically up to 8%, such as tops, dresses and t-shirts. In an embodiment the fabric contains up to 30% of the second yarn based on the weight of the fabric. This appears to give rise to a fabric which is very comfortable for making outerwear. Preferably the fabric contains up to 10%, based on the weight of the fabric, of the second yarn.

The invention also pertains to a method for manufacturing a fabric comprising taking a first yarn having a UV-A transmission of between 10 and 50% while substantially blocking UV-B transmission, taking at least a second yarn different from the first yarn, and interweaving the yarns such that the fabric is provided with regular mesh openings that give rise to a transmission of the fabric of between 20 and 65% for UV-A and between 3 and 20% for UV-B. Preferably, the yarns are interweaved via a knitting process.

The invention will be further explained by using the following examples and figures. All percentages are weight percentages unless indicated otherwise.

Example 1 describes a method for measuring the UV transmissiveness of yarns and fabrics Example 2 discloses yarns for use in a fabric according to the invention Example 3 discloses fabrics according to the invention and methods for manufacturing these fabrics

DETAILED DESCRIPTION

Example 1

Figure 1:
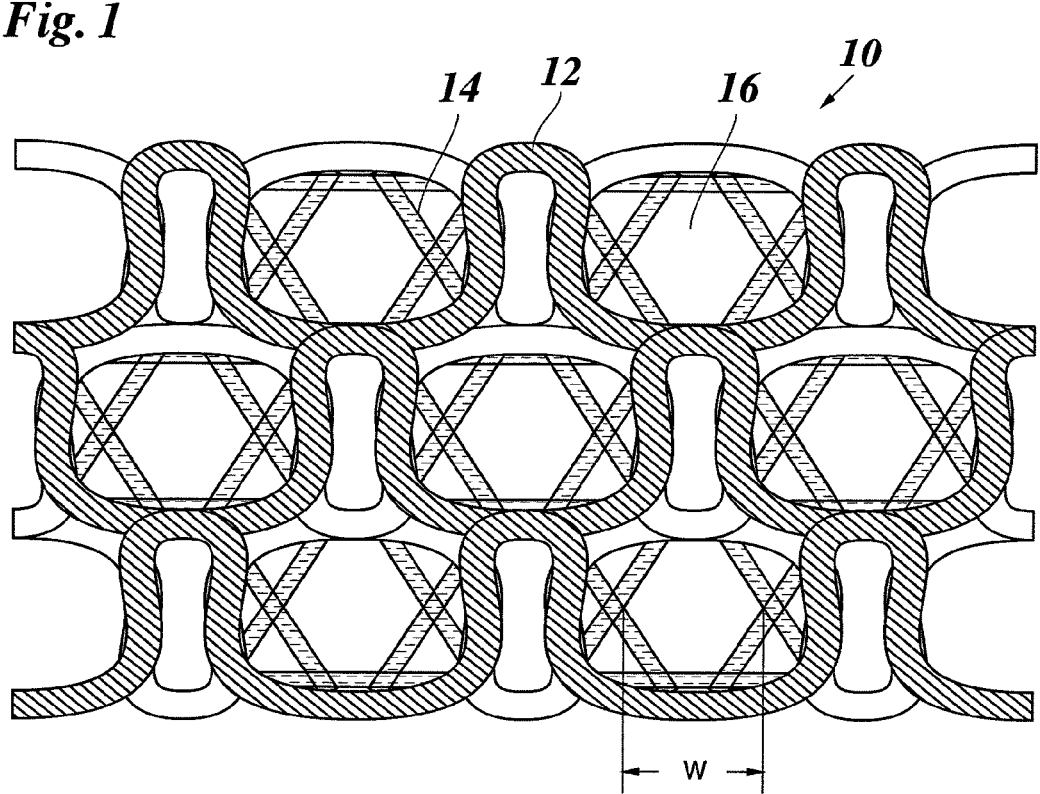
FIG. 1 is an enlarged schematic view of a circular double knitted fabric according to the invention

Measurement of UV transmission (i.e. energy intensity of UV radiation passing through versus energy intensity of incident radiation) of yarns and fabrics can be done using a spectrophotometric analyser. Such measurements have for example been described in the research disclosure called "Examination of the absorption properties of various fibres in relation to UV radiation", by Joanna Alvarez c.s., as published in AUTEX Research Journal, Vol. 3, No 2, June 2003. In the paragraph called "UV spectrophotometric method of measuring the UV penetration index" a method for determining UV transmissiveness is described using a DK-2A spectrophotometer from Beckman. The fabrics are measured as such, the yarns are measured by making a so called "Hollander Weave" of the pure yarn and measuring the resulting fabric. The Hollander Weave is type of plain weave, in this case with the warp wires of the same diameter than the weft wires. The weave is very dense with virtually no apertures, therefore, the yarns as such account for the UV radiation transmitted.

The UV transmission of the yarn is not only determined by the constituting material, e.g. the type of polyester, polyamide, polyethylene etc. but to an important extent also by parameters such as the thickness of the yarns, the number of filaments, the smoothness of the yarns (resulting in yarns ranging from "bright" to "dull"), the shape of the cross-section of the yarn (for example circular, hexagonal, square etc.) and optional additives such as brighteners added to the material of the filaments. Each of these parameters has an effect on the UV transmission. By varying these features an optimum result can be found for each application of a particular yarn to produce a particular fabric. With respect to a fabric made by interweaving various yarns, the UV transmissiveness not only depends on the type of yarns used but also on the method of interweaving, the applied dyestuff, optional additives such as softeners etc.

Example 2

Since the UV transmissive properties of the yarns, as outlined here-above, depend on many parameters and interdependencies of these parameters, the properties of suitable yarn cannot be specified simply by giving exact ranges for these parameters. This would unduly restrict the scope of the invention. Therefore, the yarns for use according to the invention are specified by the required UV transmissiveness. Relevant yarn parameters (such as material, thickness, number of filaments etc) that may influence this UV transmissiveness are disclosed under example 1, and the result of changes for these parameters can be directly and positively verified by the UV-transmission test as described here-above. With respect to a fabric made by using these yarns, the UV transmissiveness not only depends on the type of yarns used but also on the method of interweaving, the applied dyestuff, the optional use of additives etc. Therefore, with respect to the UV transmissiveness of the fabric, it is clear that this is specified also by stating the required UV transmission values.

Yarns that are transmissive for UV-A and block UV-B as specified in the appended claims are the polyester yarn type 55f20 t1001 (55Dtex, 20 filaments, bright, circular cross-section) available from Kordsa International Wilmington, Del., USA (formerly DuPont Sabanci Polyester); type 50f22 polyester yarn (55Dtex, 22 filaments, bright, circular cross section) available from Setila S.A., Valence, France; type 50f20 t625S polyester yarn (50Dtex, 20 filaments, bright, circular cross section) available from Trevira, Hattersheim, Germany and type 50f18 polyester yarn (50 Dtex, 18 filaments, bright, circular cross-section) available from Brilén, Barbastro, Spain.

Non-elastic yarns for use in the fabric according to the invention are i.a. cotton, e.g. 70/1 NM, viscose, hemp, flax etc.

Elastic yarns for use in the fabric according to the invention are i.a. elasthane yarns such as LYCRA, elastic fibre available from Invista, Whichita, USA; Dorlastan, elastic fibre available from Asahi Kasei Spandex Europe GmbH, Frankfurt, Germany and Dow XLA elastic fiber, available from Dow Fiber Solutions, United Kingdom. Other suitable yarns are Elastic Polyester available from Trevira GmbH Werk Guben, Guben, Germany and Elastic Polyester available from Weber & Heusser, Albstadt, Germany.

Corespun yarns are available i.a. from Weber & Heusser, Albstadt, Germany and Fein-Elast Umwindewerk GmbH, Lustenau, Austria. A first example is a yarn based on Dorlastan (44Dtex; 8.34 weight %) and covered with 70/1 NM combed cotton (91.66 weight %). A second example of a corespun yarn is based on LYCRA (44Dtex) and covered with polyester 50f24 (50Dtex, 24 filaments). A third example is based on Dow XLA elastic fiber (44Dtex) and covered with 50/1 NM combed cotton. A fourth example is Dorlastan (44Dtex) covered with polyester 50f24 (50Dtex, 24 filaments).

Example 3

A fabric according to the invention can be made according to any suitable interweaving method, as long as meshes are provided that lead to the UV transmission rates as specified in the appended claims. Methods usable in the present invention are for example described in "Knitting Technology: A Comprehensive Handbook and Practical Guide to Modern Day Principles and Practices" by David J. Spencer (1989). Other sources of suitable methods are for example "Wellington Sears Handbook of Industrial Textiles" by Sabit Adanur (1995) and "Handbook of Weaving" of the same author (2001).

Common types of interweaving which appear to be suitable for obtaining a fabric according to the invention are the commonly applied "weft knit", e.g. a double-knitting method (also called "double Jersey") which is typically used for circular knitting, and a "warp knit" which is typically used for flat knitting. With these types of interweaving five types of fabric which fulfil the UV transmission demands of the present invention have been made. Fabrics 1, 3 and 4 have been made as a weft knit, in particular a double Jersey knit. Fabrics 2 and 5 have been made as a warp knit.
Fabrics 1, 1': 55% combed cotton 70/1 NM; 40% 55f20 t1001 polyester yarn; 5% Corespun Dorlastan (1) or Corespun Lycra (1') as described under example 2.
Fabric 2: 80% 50f22 polyester yarn; 20% LYCRA (44Dtex, bright, type 269B)
Fabric 3: 55% uncombed cotton 70/1 NM; 45% 55f20 t1001 polyester yarn
Fabric 4: 48% combed cotton 50/1 NM; 45% polyester (50f20 of Setila S.A.); 7% Corespun XLA Dtex 44 as described under example 2
Fabric 5: 78% 55f20 polyester yarn; 22% Dow XLA Dtex 44

Fabrics 1, 1' and 4 appear to be very suitable for women's tops, dresses and T-shirts (little stretch). Fabrics 2 and 5 appear to be very suitable for swim- and bikewear (significant stretch). Fabric 3 appears to be suitable for all kinds of regular shirts, e.g. polo shirts (typically no stretch).

FIG. 1

As is shown in FIG. 1, a pique-type double knitted fabric 10 according to the invention is composed of transparent natural yarn 12, e.g. cotton, and a UV-A transmissive synthetic yarn 14, e.g. yarns as described under example 2. The fabric has regular, polygonal or almost circular mesh openings 16 with a size W in the range from 100 to 300 μm, preferably about 200 μm. As can be seen in FIG. 1, the relatively large mesh openings formed by the regular yarn 12 are partly closed or reduced in size by the synthetic yarn 14 which is effective as a UV-B filter.

FIG. 2

Figure 2:
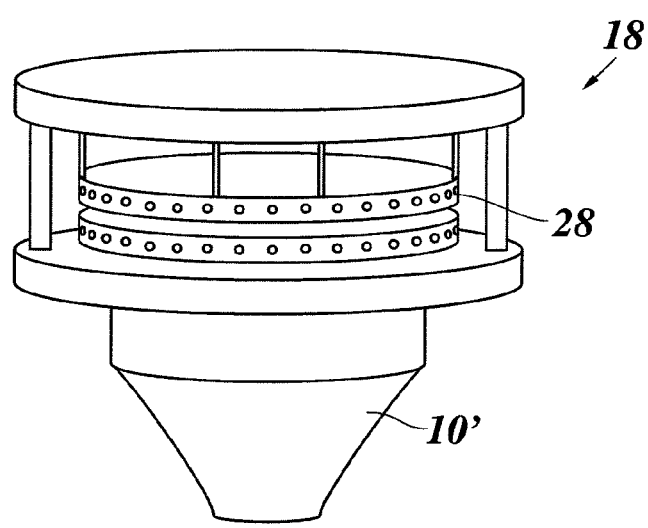
FIG. 2 is a schematic view of a circular knitting machine

The fabric 10 is manufactured in the form of a tube 10' on a circular knitting machine 18 which has schematically been shown in FIG. 2. The knitting machine has circular needle assemblies 28 with a diameter of 76.2 cm and 11 needles/cm (28 needles/inch). In a specific example, the natural yarn 12 is cotton 70/1 NM, and the synthetic yarn 14 is polyester with 55 Dtex and 20 filaments (for example: type 55f20 t1001 as mentioned under example 1).

FIG. 3

Figure 3:
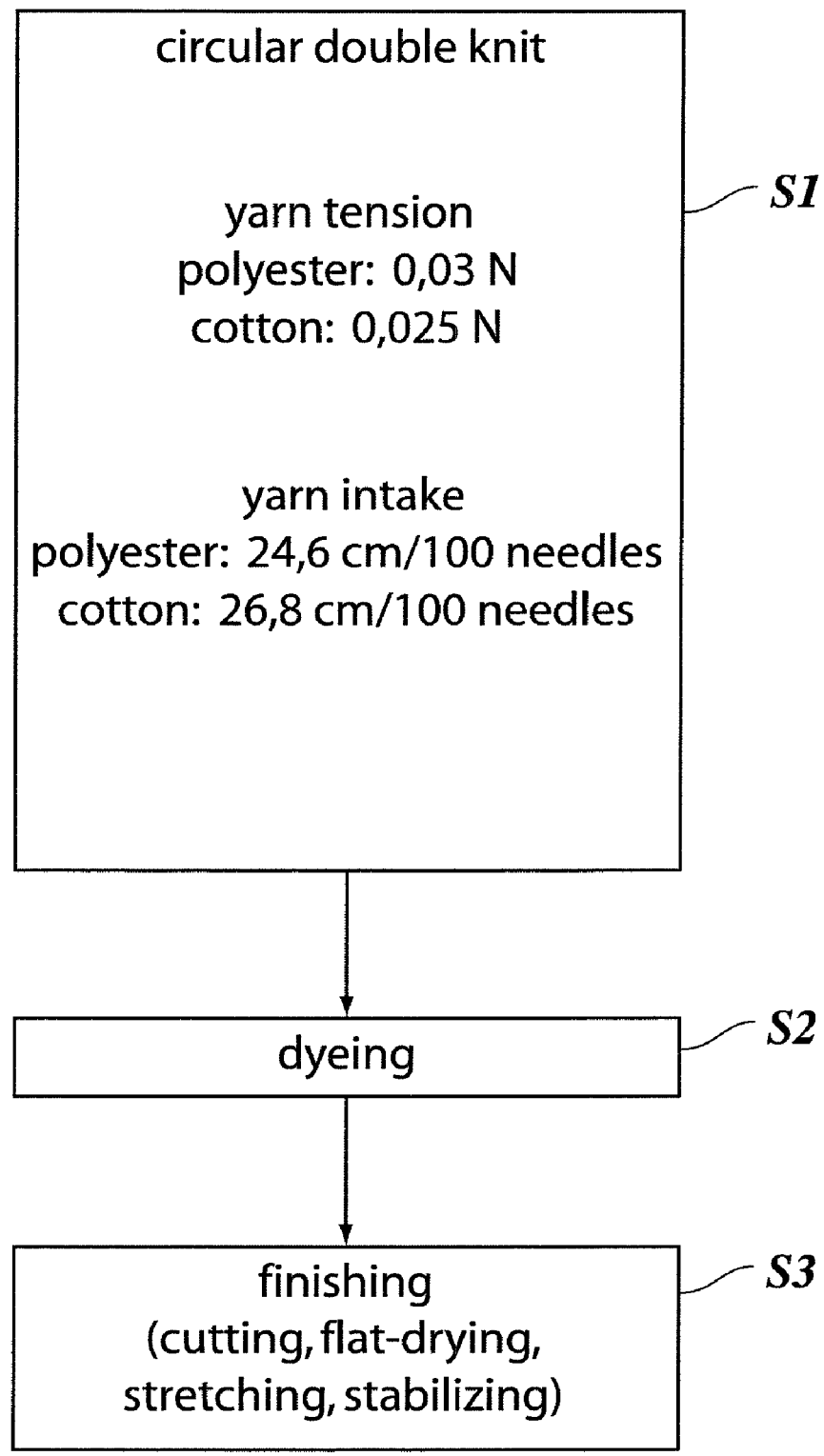
FIG. 3 is a flow diagram illustrating a manufacturing process of a fabric.

The manufacturing process for this example has diagramatically been shown in FIG. 3. In step S1 the tube 10' is knitted on the circular double knitting machine 18 with a double Jersey binding and with a yarn tension of 0.03 N for polyester and 0.025 N for cotton. The yarn intake is 24.6 cm/100 needles for polyester and 26.8 cm/100 needles for cotton. Thus, the resulting fabric will have a composition of 45% polyester and 55% cotton, and the weight before dyeing will be 98.0 g/m$^2$.

In step S2, the tube 10' is dyed in a bath process at a temperature of 130° C. with disperse dyes for the polyester yarn yarn, after which it is cooled down to 95° C. and then the cotton yarn is dyed with direct dyes. After dyeing, silicon based softeners will be added, the weight of the fabric will then be around 140.0 g/m$^2$.

In step S3, the wet, dyed fabric tube 10' is cut and flat-dried. Then, the fabric is stretched and stabilised at a temperature of 190° C.

The final product is a double knitted pique-type fabric with a weight of approximately 130 g/m$^2$. The UV-A transmission is 44% and the UV-B transmission is 12%. These figures may slightly change when the fabric is washed, but will remain at approximately 40% for UV-A and 10% for UV-B.

The invention claimed is:
1. A fabric comprising:
a first yarn having an ultraviolet radiation transmission in the UV-A range of 320-400 nm of between 10 and 50% while substantially blocking an ultraviolet radiation transmission in the UV-B range of 290-320 nm, and
at least a second yarn different from the first yarn,
the yarns being interweaved such that the fabric has regular mesh openings, and
both the first yarn and the mesh openings together control transmission of the fabric of between 20 and 65% for ultraviolet radiation transmission in said UV-A range and between 3 and 20% for ultraviolet radiation transmission in said UV-B range.
2. A fabric according to claim 1, wherein the ultraviolet radiation transmission in said UV-A range of the fabric is between 25 and 60% and the ultraviolet radiation transmission in said UV-B range is between 5 and 15%.

3. A fabric according to claim 2, wherein the ultraviolet radiation transmission in said UV-A range of the fabric is between 30 and 45% and the ultraviolet radiation transmission in said UV-B range is between 10 and 12%.

4. A fabric according to claim 1, wherein the second yarn is a non-elastic yarn.

5. A fabric according to claim 4, wherein the first and second yarn are interweaved via a double-knitting process.

6. A fabric according to claim 4, wherein the content of the non-elastic yarn is between 15 and 85%, based on the total weight of the fabric.

7. A fabric according to claim 4, wherein the weight of the fabric is between 90 and 180 g/m².

8. A fabric according to claim 3, wherein the second yarn is an elastic yarn.

9. A fabric according to claim 8, wherein the second yarn is a naked yarn, and the content of the second yarn is between 10 and 30% based on the total weight of the fabric.

10. A fabric according to claim 9, wherein the fabric contains 30-50% of the first yarn, and up to 60% of a third yarn, the third yarn being non-elastic.

11. A fabric according to claim 8, wherein the second yarn is a corespun yarn.

12. A fabric according to claim 11, wherein the fabric contains up to 30% of the second yarn based on the weight of the fabric.

13. A fabric according to claim 12, wherein the fabric contains up to 10% of the second yarn.

14. A method for manufacturing a fabric comprising the steps of:
   taking a first yarn having an ultraviolet radiation transmission in the UV-A range of 320-400 nm of between 10 and 50% while substantially blocking an ultraviolet radiation transmission in the UV-B range of 290-320 nm,
   taking at least a second yarn different from the first yarn, and
   interweaving the yarns such that the fabric is provided with regular mesh openings and such that both the first yarn and the mesh openings together control transmission of the fabric of between 20 and 65% for ultraviolet radiation transmission in said UV-A range and between 3 and 20% for ultraviolet radiation transmission in said UV-B range.

15. A method according to claim 14, wherein the yarns are interweaved via a knitting process.

16. A garment made with a fabric comprising:
   a first yarn having an ultraviolet radiation transmission in the UV-A range of 320-400 nm of between 10 and 50% while substantially blocking an ultraviolet radiation transmission in the UV-B range of 290-320 nm, and
   at least a second yarn different from the first yarn,
   the yarns being interweaved such that the fabric has regular mesh openings, and
   both the first yarn and the mesh openings together control transmission of the fabric of between 20 and 65% for ultraviolet radiation transmission in said UV-A range and between 3 and 20% for ultraviolet radiation transmission in said UV-B range.

17. A fabric according to claim 6, wherein the content of the non-elastic yarn is between 50 and 60%, based on the total weight of the fabric.

18. A fabric according to claim 7, wherein the weight of the fabric is between 125 and 150 g/m².

19. A fabric according to claim 9, wherein the content of the second yarn is around 20% based on the total weight of the fabric.

* * * * *